United States Patent
Maack

(10) Patent No.: US 10,463,323 B2
(45) Date of Patent: Nov. 5, 2019

(54) DETECTOR ROTATION CONTROLLED BY X-RAY COLLIMATION

(71) Applicant: KONINKLIJKE PHILIPS N.V., Eindhoven (NL)

(72) Inventor: Hanns-Ingo Maack, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 176 days.

(21) Appl. No.: 15/518,249

(22) PCT Filed: Oct. 9, 2015

(86) PCT No.: PCT/EP2015/073480
§ 371 (c)(1),
(2) Date: Apr. 11, 2017

(87) PCT Pub. No.: WO2016/058957
PCT Pub. Date: Apr. 21, 2016

(65) Prior Publication Data
US 2017/0303879 A1    Oct. 26, 2017

(30) Foreign Application Priority Data

Oct. 13, 2014    (EP) .................................. 14188653

(51) Int. Cl.
*A61B 6/00* (2006.01)
*G21K 1/02* (2006.01)
(Continued)

(52) U.S. Cl.
CPC .............. *A61B 6/4233* (2013.01); *A61B 6/06* (2013.01); *A61B 6/4452* (2013.01); *A61B 6/545* (2013.01); *G21K 1/04* (2013.01)

(58) Field of Classification Search
CPC ......... A61B 6/06; A61B 6/4233; A61B 6/485; A61B 6/542; A61B 6/52; A61B 6/469
See application file for complete search history.

(56) References Cited

U.S. PATENT DOCUMENTS

| 6,259,767 B1 | 7/2001 | Nemann et al. |
| 2003/0095627 A1 | 5/2003 | Anderton |

(Continued)

FOREIGN PATENT DOCUMENTS

| EP | 1444952 A1 | 8/2004 |
| JP | 2005000372 A | 1/2005 |

(Continued)

*Primary Examiner* — Don K Wong
(74) *Attorney, Agent, or Firm* — Larry Liberchuk

(57) ABSTRACT

The present invention relates to a rotatable X-ray detector. In order to improve clinical workflow, an X-ray detector arrangement (10) is provided that comprises an X-ray detector unit (12) and a rotation unit (14). The X-ray detector unit (12) comprises an X-ray detector (16) with a plurality of X-ray detecting elements arranged as a detector surface (18). The rotation unit (14) is configured to rotate the X-ray detector about an axis (20) perpendicular to the detecting surface (18) at least at a point of intersection with the detector surface (18) upon receiving a rotation signal (22). Further, the rotation signal (22) is dependently ruled by a collimator configuration of an X-ray source arrangement for providing X-ray radiation towards the X-ray detector unit.

8 Claims, 5 Drawing Sheets

(51) Int. Cl.
*A61B 6/06* (2006.01)
*G21K 1/04* (2006.01)

(56) References Cited

U.S. PATENT DOCUMENTS

| | | | |
|---|---|---|---|
| 2007/0147576 A1 | 6/2007 | Yamazaki | |
| 2012/0155615 A1 | 6/2012 | Liu | |
| 2013/0058462 A1* | 3/2013 | Jenkins | G21K 1/04 378/147 |
| 2013/0336449 A1 | 12/2013 | Tanabe | |

FOREIGN PATENT DOCUMENTS

| | | |
|---|---|---|
| JP | 2010051727 A | 3/2010 |
| RU | 2004111027 A | 10/2005 |
| WO | 2014143162 A1 | 9/2014 |

\* cited by examiner

DETECTOR ROTATION CONTROLLED BY X-RAY COLLIMATION

CROSS-REFERENCE TO PRIOR APPLICATIONS

This application is the U.S. National Phase application under 35 U.S.C. § 371 of International Application No. PCT/EP2015/073480, filed on Oct. 9, 2015, which claims the benefit of European Patent Application No. 14188653.1, filed on Oct. 3, 2014. These applications are hereby incorporated by reference herein.

FIELD OF THE INVENTION

The present invention relates to a rotatable X-ray detector, and in particular relates to an X-ray detector arrangement, to an X-ray image acquisition system, to a method for aligning a detector, to a computer program element and to a computer readable medium.

BACKGROUND OF THE INVENTION

For the detection of X-ray radiation, X-ray detectors with different sizes and formats are provided. The X-ray detectors on the market today usually have a square or rectangular shape. Dependent on the nature of the target being X-rayed, the X-ray detectors with a rectangular shape can be placed in a landscape or portrait position. The X-ray detectors can also be rotated by other degrees in order to be adapted to different anatomical conditions. For the rotation of the X-ray detector, the current workflow requires a lab technician to rotate the X-ray detector manually with a kind of lever arm, or to press a "rotation button", thus enabling a motorized rotation of the X-ray detector. This, however, results in extra workflow steps and increases the workload of the medical staff.

U.S. Pat. No. 6,259,767 B1 describes an X-ray device having an adjustable diaphragm aperture to present an exposure field on an X-ray image detection device. The size of the exposure field is correlated to an organ or to a body region to be imaged by using a set of exposure parameters associated with the organ or the body region.

SUMMARY OF THE INVENTION

There may be a need to provide an X-ray imaging system to improve the clinical workflow.

The object of the present invention is solved by the subject-matter of the independent claims, wherein further embodiments are incorporated in the dependent claims. It should be noted that the following described aspects of the invention apply also for the X-ray detector arrangement, the X-ray image acquisition system, the method for aligning a detector, the computer program element and the computer readable medium.

According to the present invention, an X-ray detector arrangement is provided that comprises an X-ray detector unit and a rotation unit. The X-ray detector unit comprises an X-ray detector with a plurality of X-ray detecting elements arranged as a detector surface. The rotation unit is configured to rotate the X-ray detector, relative to the X-ray detector unit, about an axis perpendicular to the detector surface at least at a point of intersection with the detector surface upon receiving a rotation signal that is dependently ruled by a collimator configuration of an X-ray source arrangement for providing X-ray radiation towards the X-ray detector unit.

As an advantage, a manual rotation of the detector unit with a kind of lever arm or a motorized rotation of the detector unit with a "rotation button" is not required. In other words, no explicit user action or user interface is needed to rotate the detector. A user can simply modify the collimator configuration to define the size, shape and/or orientation of the radiation field and the detector unit rotates to match the collimator configuration automatically.

In an example, the detector surface is a plane surface or a flat surface.

In another example, the detector surface is a curved surface.

It is noted that the axis may be a physical shaft of the rotation, but the primary meaning is a mathematical or virtual axis through the point of intersection.

According to an example, the rotation signal is provided as a master-to-slave command signal. The rotation unit is configured to be a slave unit to receive the master-to slave command signal.

In other words, the collimator is a master device of a master/slave system and the X-ray detector rotates to match the collimator configuration; the detector is a slave device of the master/slave system.

According to an example, the rotation signal is provided to control the rotation unit to rotate the X-ray detector at least from a first rotation position to a second rotation position. An angular displacement between the second rotation position and the first rotation position is determined by the rotation signal.

In other words, the rotation signal may not only initiate the rotation action of the X-ray detector, but also determine the angular displacement, i.e. the angle through which the X-ray detector rotates. As a result, the X-ray detector acts in a role of a slave unit. The rotation of the X-ray detector is triggered by the rotation signal that also sets the stop position of the X-ray detector.

According to an example, the X-ray detector has a shape with a first extension and a second extension. The first extension is larger than the second extension. In the second rotation position, the first extension and the second extension are arranged in the angular displacement relative to the first extension and the second extension in the first rotation position. Preferably, the X-ray detector has a rectangular shape.

The X-ray detector may vary in shape. For example, the X-ray detector is oval or elliptic in shape. For example, the X-ray detector has a rhombic form. Preferably, the X-ray detector is rectangular.

According to an example, the collimator configuration comprises at least one of the group of: dimensions of a collimator opening; collimator position; collimator orientation; and dimensions of the collimation in the detector plane.

According to the present invention, also an X-ray image acquisition system is provided that comprises an X-ray source arrangement and an X-ray detector arrangement. The X-ray source arrangement comprises an X-ray source unit, a collimator unit and a control unit. The X-ray source unit is configured to generate X-ray radiation towards the X-ray detector arrangement. The collimator comprises a collimator opening having adjustable dimensions to adjust a shape of the X-ray radiation beam passing the collimator opening. The control unit is configured to detect the collimator configuration and to provide in response the rotation signal to the rotation unit. The rotation unit rotates the X-ray detector based on the rotation signal such that a rotation position of the X-ray detector matches the collimator configuration.

In other words, the collimator unit is the master of the rotation position of the X-ray detector.

As an advantage, adjusting the collimation is the master of the workflow and no user interaction is required to rotate the X-ray detector. As a result, the work load of the medical staff is reduced and the clinical workflow is improved.

According to an example, the collimator unit is at least a part of a master unit, and the X-ray detector unit is at least a part of a slave unit.

For example, the collimator unit is a master unit of the X-ray detector unit being a slave unit.

According to an example, the control unit is configured to detect a geometry of a collimation field on the detector surface based on the collimator configuration. The geometry comprises a primary extension and a secondary extension, which is transverse to the primary extension. The primary extension is larger than the secondary extension. The detector surface has a shape with a primary detector extension and a secondary detector extension, and the primary detector extension is larger than the secondary detector extension. The control unit is configured to evaluate a geometric relationship between the detected collimation field and the detector surface and to provide in response the rotation signal to the rotation unit. The rotation unit is configured to rotate the X-ray detector based on the rotation signal such that the collimation field is confined to the shape of the detector surface.

For example, the control unit compares the geometries of the collimator field and the detector surface and determines whether the collimation field is confined to the shape of the detector surface. If not, the control unit provides a rotation signal informing the rotation unit to rotate the X-ray detector to match the collimation field. This ensures that the X-ray radiation is limited to expose the detector surface and not more.

According to an example, upon a change of the collimator configuration, the control unit detects a deviation between a current detected collimator configuration and a previously detected collimator configuration and provides in response a further or updated signal of the rotation signal to the rotation unit. The rotation unit is configured to rotate the X-ray detector based on the further or updated signal of the rotation signal such that a current rotation position of the X-ray detector matches the current detected collimator configuration again.

As a result, the rotation position of the X-ray detector follows the change of the collimator configuration continuously.

According to an example, the control unit is configured to store at least collimator configuration parameters together with operating parameters of the X-ray detector arrangement.

For example, the operating parameters may comprise detector rotation position data, detector position data, or dimensions of the detector. In this way, the geometric relationship can be detected by comparing the collimator configuration parameters and the operating parameters of the X-ray detector.

According to an example, the control unit is configured to set the maximum dimensions of the collimator opening such that the dimensions of the collimation field are smaller than the dimensions of the detector surface.

According to an example, the control unit is configured to detect a spatial displacement between the X-ray source arrangement and the X-ray detector arrangement. A moving assembly is provided performing a relative movement for bringing the X-ray detector arrangement in alignment with the X-ray source arrangement based on the detected spatial displacement.

According to the present invention, also a method for aligning a detector is provided, comprising the following steps:
a) adjusting a configuration of a collimator of an X-ray source arrangement;
b) detecting the adjusted collimator configuration;
c) providing a rotation signal to a rotation unit; wherein the rotation signal is based on the detected adjusted collimator configuration; and
d) rotating an X-ray detector according to the rotation signal.

According to the present invention, a computer program element for controlling an apparatus is provided, which, when executed by a processing unit, is adapted to perform the method steps.

According to the present invention, a computer readable medium having stored the program element discussed previously is provided.

According to an aspect, an X-ray detector is configured to be a slave unit of a collimator being a master unit. The changes of a collimator configuration, such as dimensions of the adjustable opening of the collimator, orientation of the collimator and/or position of the collimator are determined and the X-ray detector rotates accordingly to match this collimator configuration. In other words, the collimator is the master of the X-ray detector position. For example, when an X-ray detector is in a landscape orientation, it is allowed to set the collimator to a portrait orientation. The detector then rotates to match this setting accordingly by e.g. rotating 90° to be in the portrait orientation. Since no user interaction is required in the process of the X-ray detector rotation, the number of workflow steps for the medical staff is reduced and an improved clinical workflow is achieved.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
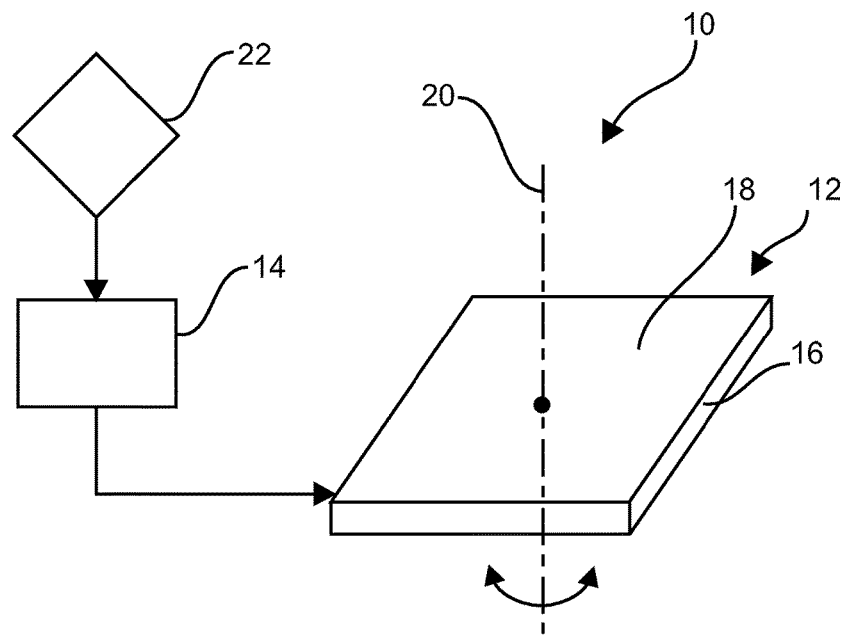
FIG. 1 shows an exemplary embodiment of an X-ray detector arrangement according to the present invention.

FIG. 1 shows an exemplary embodiment of an X-ray detector arrangement 10. The X-ray detector arrangement 10 comprises an X-ray detector unit 12 and a rotation unit 14. The X-ray detector unit 12 comprises an X-ray detector 16 with a plurality of X-ray detecting elements arranged as a detector surface 18. The rotation unit 14 is configured to rotate the X-ray detector 16 about an axis 20 perpendicular to the detector surface 18 at least at a point of intersection with the detector surface 18 upon receiving a rotation signal 22. The rotation signal 22 is dependently ruled by a collimator configuration of an X-ray source arrangement for providing X-ray radiation towards the X-ray detector unit 12.

In an example, the rotation signal 22 is provided as a master-to-slave command signal, and the rotation unit 14 is configured to be a slave unit to receive the master-to-slave command signal.

In an example, the collimator configuration comprises at least one of the group of dimensions of a collimator opening, collimator position, collimator orientation and/or dimensions of the collimation in the detector plane.

The detector surface 18 may be a plane surface or a flat surface. In another example, the detector surface 18 is a curved surface.

The X-ray detector 16 may have different formats. In an example, the X-ray detector 16 is a detector supported by the X-ray detector unit 12, such as a rigid detector that is permanently installed inside a tray, e.g. a Bucky tray. In another example, the X-ray detector 16 is a portable detector that is temporarily supported by the X-ray detector unit 12, such as a portable detector that can be taken out of the tray by a user. In another example, the X-ray detector 16 is a cassette with an X-ray film screen.

The X-ray detector 16 may also be arranged in a housing that may have a square or rectangular shape and the image matrix may be rectangular. In an example, the rotation unit 14 is configured to rotate the X-ray detector 16 inside the housing. In another example, the rotation unit 14 is configured to rotate the X-ray detector 16 together with the housing.

The term "perpendicular" refers to an angle of approximately 90°, comprising a deviation of +/−15° for example.

The term "dependently ruled" refers to a signal that is controlled by the collimator configuration to an essential extent. For example, if the collimator configuration is changed or adapted, also the rotation signal is changed or amended accordingly.

Figure 2:
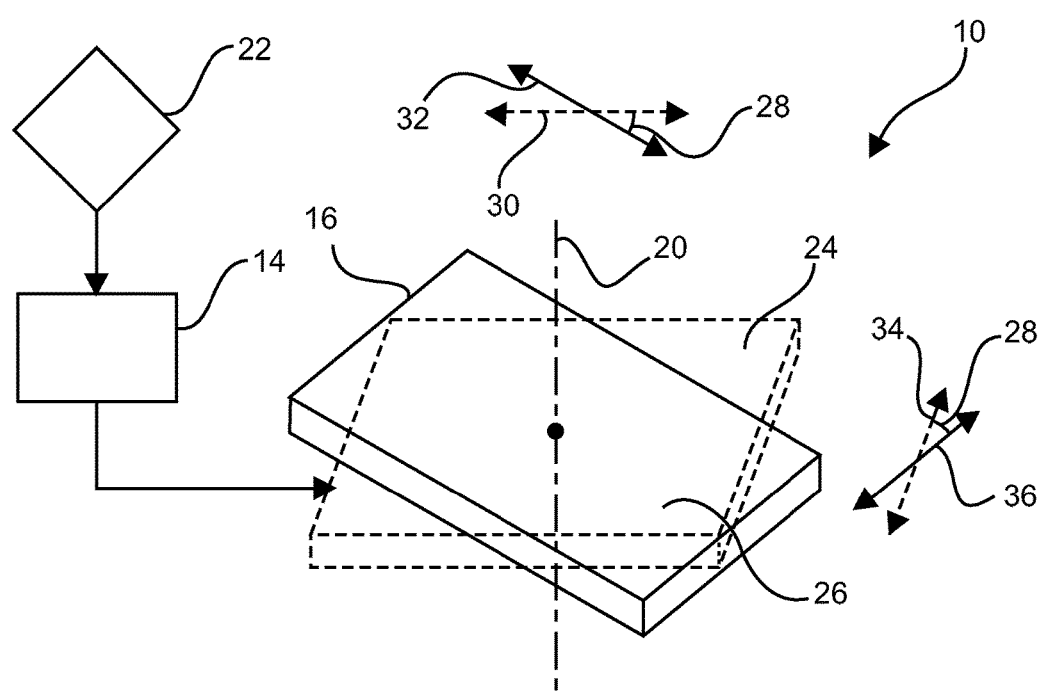
FIG. 2 shows a further exemplary embodiment of the X-ray detector arrangement in two different rotation positions according to the present invention.

FIG. 2 shows a further exemplary embodiment of the X-ray detector arrangement 10 in two different rotation positions.

The rotation signal 22 is provided to control the rotation unit 14 to rotate the X-ray detector 16 at least from a first rotation position 24 to a second rotation position 26. An angular displacement 28 between the second rotation position 26 and the first rotation position 24 is determined by the rotation signal 22.

The rotatable X-ray detector 16 has a shape with a first extension, indicated by first arrows 30, 32, and a second extension, indicated by second arrows 34, 36. The first extension 30, 32 is larger than the second extension 34, 36. In an example, the X-ray detector 16 has a rectangular shape with rounded corner sections. In another example, the X-ray detector 16 has an oval or elliptic shape. In another example, the X-ray detector 16 has a rhombic shape. Preferably, the X-ray detector 16 has a rectangular shape. The X-ray detector 16 may also have a hand grip for allowing free manual positioning relative to an imaged object.

In the second rotation position 26, the first extension 32 and the second extension 36 are arranged in the angular displacement 28 relative to the first extension 30 and the second extension 34 in the first rotation position. It is noted that the term "arranged" relates e.g. to the rotation of the first and second extensions according to the angular displacement 28.

The angular displacement 28 is indicated by the angle between the first extension 30 in the first rotation position 24 and the first extension 32 in the second rotation position 26. Alternatively, the angular displacement 28 is indicated by the angle between the second extension 34 in the first rotation position 24 and the second extension 36 in the second rotation position 26. In an example, the second rotation position 26 is perpendicular to the first rotation position 24, in other words, the angular displacement is +/−90°. In another example, the angular displacement 28 is arbitrary, such as 10°, 15°, 30°, 45°, 60° or 75°, or a different value. The value of the angular displacement 28 is determined in such a manner that the X-ray detector 16 can be rotated to achieve a better match with a patient's anatomy. For example, the value may be determined by how an organ, such as a hand, is placed on the table.

Figure 3A:
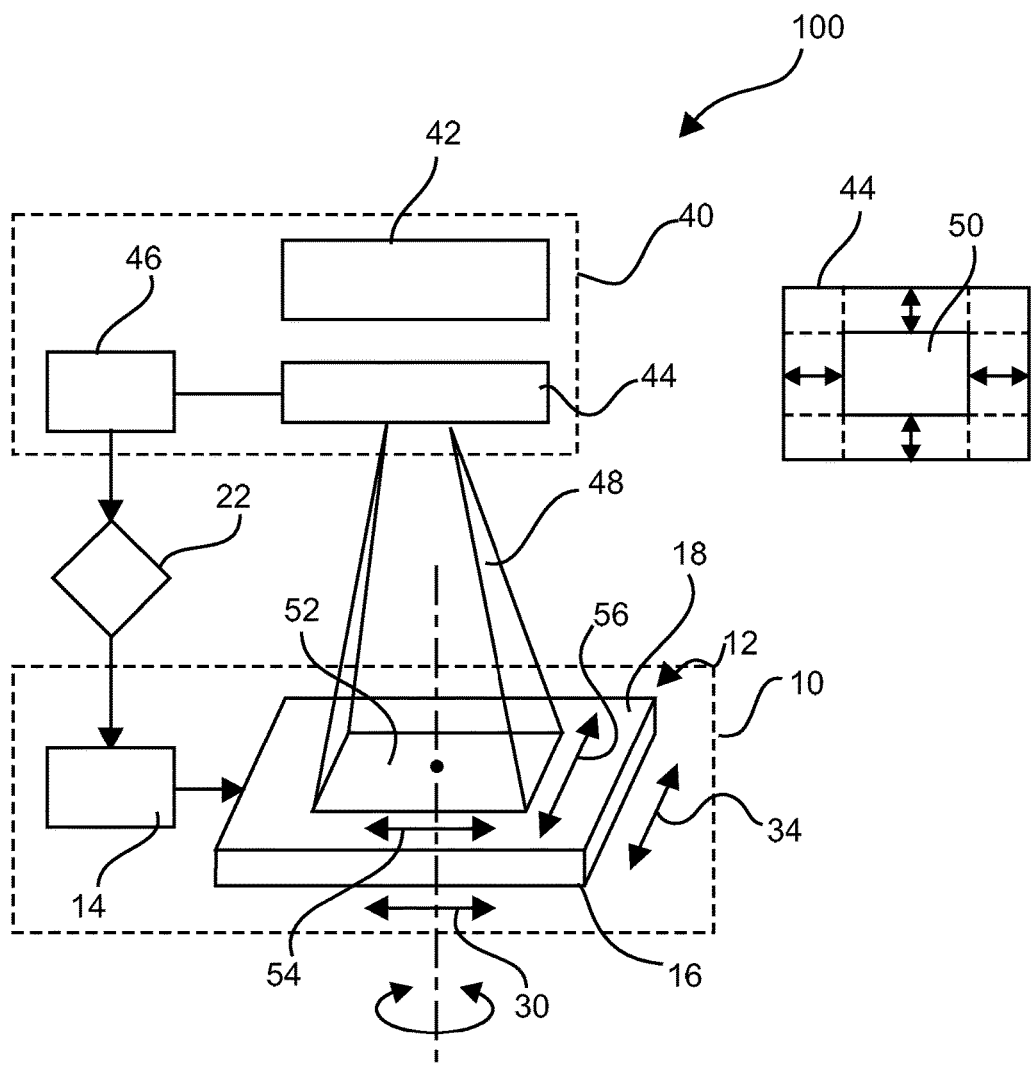
FIG. 3A shows an exemplary embodiment of an X-ray image acquisition system according to the present invention.

In an example, the rotation is exactly 90°. In another example, the rotation is provided with much smaller values to adapt for small rotations with odd degrees. FIG. 3A shows an exemplary embodiment of an X-ray image acquisition system 100. The X-ray image acquisition system 100 comprises an X-ray source arrangement 40 and the X-ray detector arrangement 10.

The X-ray source arrangement 40 comprises an X-ray source unit 42, a collimator unit 44 and a control unit 46. The X-ray source unit 42 and the collimator unit 44 may be connected by any suitable ways including, for example, a bearing allowing a rotation of the collimator unit 44. The X-ray detector arrangement 10 is provided as one of the above-mentioned examples of the X-ray detector arrangement 10 and comprises the X-ray detector unit 12 and the rotation unit 14. The X-ray source unit 42 is configured to generate X-ray radiation 48 towards the X-ray detector arrangement 10. The collimator unit 44 comprises a collimator opening 50 having adjustable dimensions to adjust a shape of the X-ray radiation 48 passing the collimator opening 50. The control unit 46 is configured to detect the collimator configuration and to provide in response the rotation signal 22 to the rotation unit 14. Based on the rotation signal 22 the rotation unit 14 rotates the X-ray detector 16 such that a rotation position of the X-ray detector 16 matches the collimator configuration.

According to an example, the collimator unit 44 is at least a part of a master unit, and the X-ray detector unit 12 is at least a part of a slave unit.

In an example, the geometrical parameters such as the source image distance, SID, and the source collimator distance, SCD, are provided to the control unit and the control unit 46 can calculate the dimension of the collimated area in the detector plane.

The collimator configuration may be adjusted manually or automatically. In an example, a collimator user interface is provided to control the collimator configurations. For example, wheels are provided for changing the dimensions of the collimator opening 50. Alternatively to the wheels, buttons are used to control the dimensions of the collimator opening 50. In another example, no collimator user interface is provided. Instead, the geometry, such as size, shape and orientation, of patient's anatomy may be detected by cameras, such as range cameras, optical cameras or ultrasound cameras. Anatomic landmarks may be derived from the image data to determine the collimator configuration such as dimensions of the opening, orientation of the collimator and/or position of the collimator so as to adapt the radiation field to the patient's anatomy.

Based on the collimator configuration, the control unit 46 is configured to detect a geometry of a collimation field 52 on the detector surface 18. The geometry comprises a primary extension, indicated by an arrow 54, and a secondary extension, indicated by an arrow 56, which is transverse to the primary extension. The primary extension is larger than the secondary extension.

Further, the detector surface 18 has a shape with the first detector extension, indicated by the arrow 30, and the second detector extension, indicated by the arrow 34. The first detector extension is larger than the second detector extension.

The control unit 46 is configured to evaluate a geometric relationship between the detected collimation field 52 and the detector surface 18 and to provide in response the rotation signal to the rotation unit 14. Based on the rotation signal, the rotation unit 14 rotates the X-ray detector 16 such that the collimation field 52 is limited within the detector surface 18.

The term "evaluate" relates to determination or calculation of the geometric relationship.

For example, in response to the rotation signal, the rotation unit 14 rotates the X-ray detector 16 to a rotation position such that the primary 54 and/or secondary 56 extensions of the collimation field 52 are brought into alignment with the first 30 and/or second 34 detector extensions of the detector surface 18, respectively.

According to a further example, upon a change of the collimator configuration, the control unit 46 detects a deviation between a current detected collimator configuration and a previously detected collimator configuration and provides in response a further or updated signal of the rotation signal 22 to the rotation unit 14. The rotation unit 14 rotates the X-ray detector 16 based on the further rotation signal such that a current rotation position of the X-ray detector 16 matches the current detected collimator configuration again. In other words, the X-ray detector 16 may be continuously rotated to match the collimator configuration. This will ensure that the slave unit, i.e. the rotation unit 14, follows the collimator configuration continuously.

The term "geometric relationship" refers to relationships between dimensions, shape, and/or orientation.

The geometric relationship between the collimation field 52 and the detector surface 18 may be determined in several ways. According to an example, the control unit 46 is configured to store at least the collimator configuration parameters together with operating parameters of the X-ray detector arrangement 10. In an example, the operating parameters comprise detector rotation position data, detector position data, or dimensions of the detector. The geometric relationship may thus be determined by comparing the collimator configuration parameters and the operating parameters of the X-ray detector arrangement 10.

The term "deviation" may refer to a situation where the collimation field 52 is not covered by the detector surface 18 after the adjustment of the collimator configuration. Several reasons may lead to such a situation. In an example, the dimensions of the collimator opening 50 are altered, for example, from a landscape size to a portrait size. In another example, the collimator unit 44 is rotated by a certain degree with the purpose of matching the patient's anatomy. In another example, the shape of the collimation field 52 is changed from a square shape to a rectangular shape.

The term "deviation" may also refer to a situation where after the adjustment of the collimator configuration, the collimation field 52 is still within the detector surface 18 but is no longer aligned with the detector surface 18. For example, the collimator unit is rotated by a small angle in order to be aligned with a patient's anatomy.

According to an example, the control unit 46 is further configured to set the maximum dimensions of the adjustable collimator opening 50 such that the dimensions of the collimation field 52 is smaller than the dimensions of the detector surface 18. In an example, the detector surface 18 has a rectangular shape, and the maximum dimensions relate to the size of the rectangular shape of the detector surface 18. The control unit 46 provides the rotation signal 22 once the collimator configuration is adjusted.

During the rotation and in the time interval when the collimation field 52 and the detector surface 18 do not match, the generation of X-ray radiation may be disabled. After the rotation, the X-ray generation may be enabled again.

For the matching, the primary extension 54 and the secondary extension 56 are aligned with the primary detector extension 30 and the secondary detector extension 34.

Figure 3B:
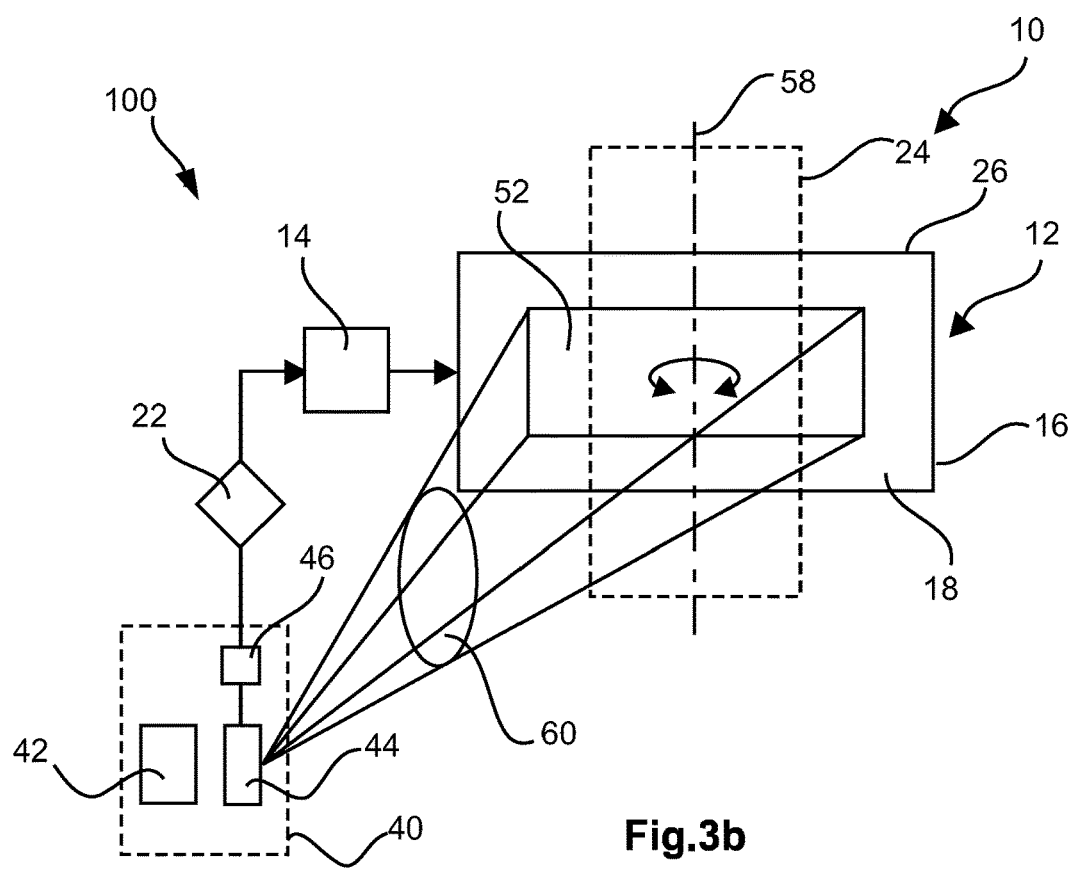
FIG. 3B shows a further exemplary embodiment of the X-ray image acquisition system with a rotated X-ray detector adaptive to a collimator configuration according to the present invention.

FIG. 3B shows a further exemplary embodiment of the X-ray image acquisition system with a rotated X-ray detector adaptive to a collimator configuration.

In the first rotational position 24, i.e. in the first orientation, the primary detector extension, i.e. the longer detector extension, is arranged parallel to a reference line 58; and in the second rotational position 26, i.e. in the second orientation, the primary detector extension, i.e. the longer detector extension, is arranged perpendicular to the reference line 58. The first position 24 is also referred to as a "portrait orientation", and the second position 26 is also referred to as a "landscape orientation".

In case of vertical X-ray radiation, the term "reference line" refers to a direction of a patient support (patient table), or to an orientation, i.e. extension, of a patient under examination. In case of horizontal X-ray radiation, the term "reference line" may relate to a horizontal line.

In this embodiment, even when the X-ray detector 16 is in the first rotation position 24, i.e. in a portrait orientation, it is allowed to set the collimator configuration to a landscape size, which thus defines the collimation field 52 in a landscape orientation for matching the geometry of the region of interest 60, such as limbs, torso, neck head, shoulder, etc. Upon change of the collimator configuration, the control unit 46 evaluates the geometric relationship between the collimation field 52 and the detector surface 18 in the first rotation position 24. Once a deviation is detected, the control unit 46 sends a further or updated signal of the rotation signal 22 to the rotation unit 14, thus activating a respective rotation to correct the rotation position of the X-ray detector 16 for bringing the X-ray detector 16 into the second rotation position 26, i.e. in a landscape orientation, so that the collimation field 52 is within the X-ray detector surface 18.

During the rotation, the generation of X-ray radiation is disabled by the control unit 46. The X-ray generation is enabled again by the control unit 46 after the rotation.

Figure 3C:
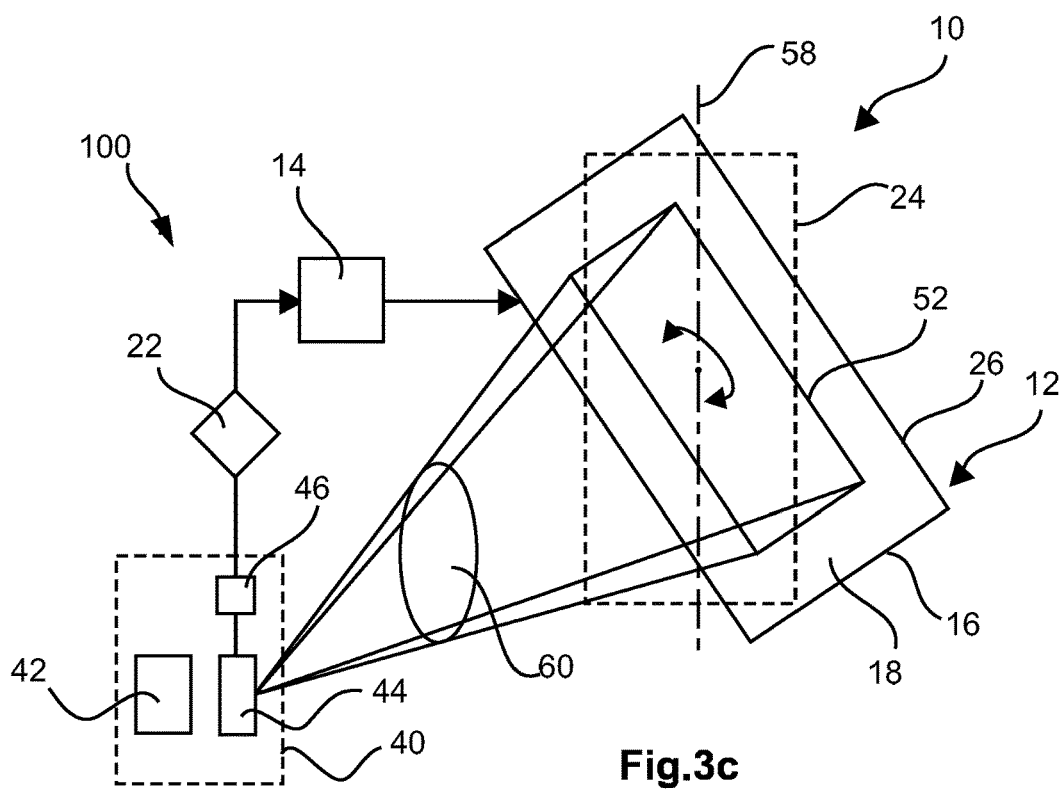
FIG. 3C shows a further exemplary embodiment of the X-ray image acquisition system with a rotated X-ray detector adaptive to another collimator configuration according to the present invention.

FIG. 3C shows a further exemplary embodiment of the X-ray image acquisition system 100 with a rotated X-ray detector adaptive to another collimator configuration.

In this embodiment, the collimator unit 44 is rotated by an arbitrary degree, for example, to achieve a better match with a region of interest 60, like a patient's anatomy. Due to the orientation of the collimation field 52, the collimation field 52 cannot be covered by the X-ray detector surface 18 in the first orientation position 24. This deviation is detected by the control unit 46. According to the collimator configuration, the control unit 46 further determines an angular displacement and transmits the rotation signal 22 to the rotation unit 14. Upon receiving the rotation signal 22, the rotation unit 14 rotates the X-ray detector 16 from the first rotation position 24 to the second rotation position 26 by the angular displacement so that the collimation field 52 is recovered by the X-ray detector surface 18.

The generation of X-ray radiation is disabled during the rotation by the control unit 46. After the rotation, the X-ray generation is enabled again by the control unit 46.

Figure 4:
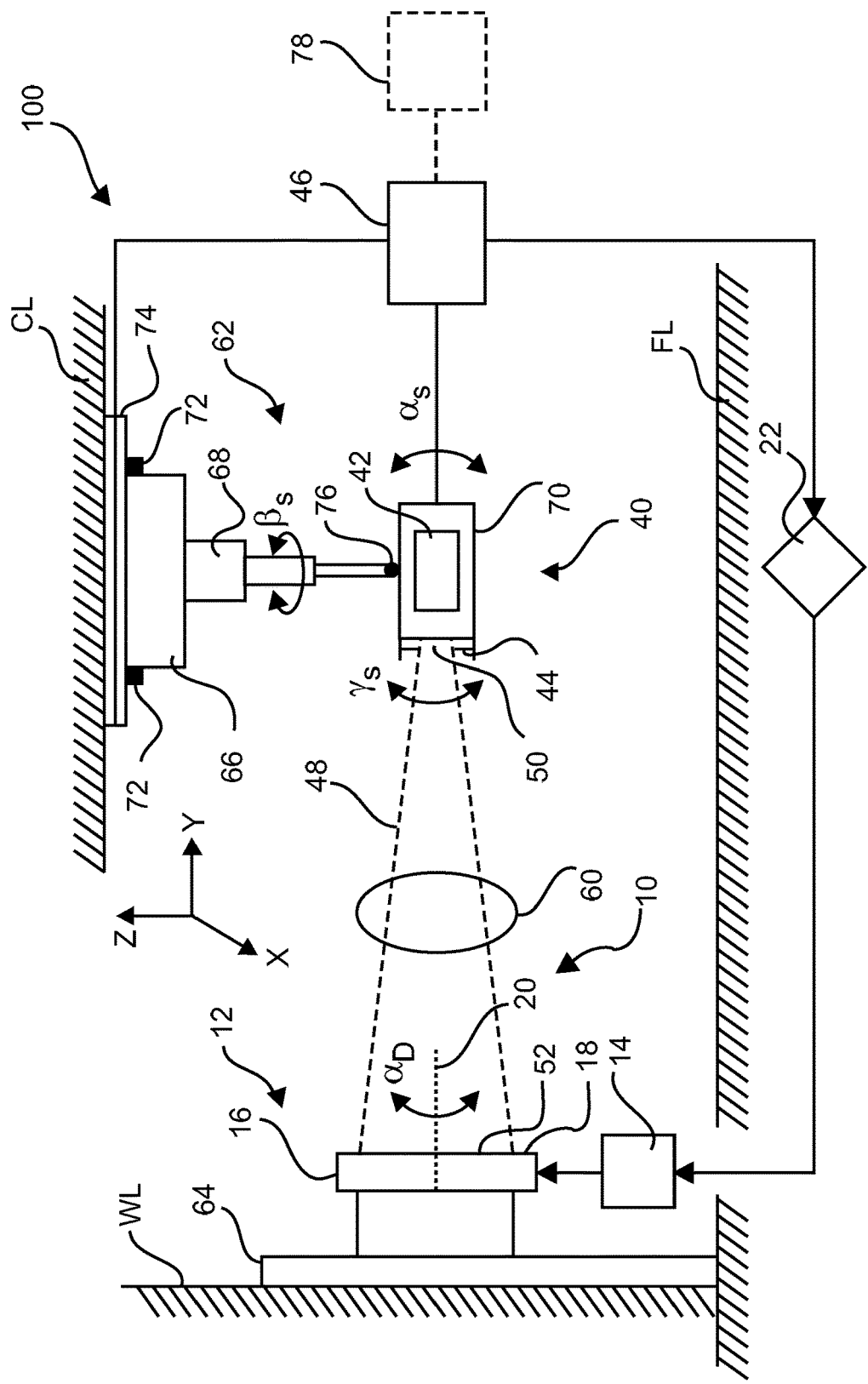
FIG. 4 shows a further exemplary embodiment of the X-ray image acquisition system in an examination room according to the present invention.

FIG. 4 shows a further exemplary embodiment of the X-ray image acquisition system 100 in an examination room. The examination room is indicated schematically by a floor FL, a ceiling CL and one of walls WL. The X-ray image acquisition system 100 is shown with the X-ray source arrangement 40 comprising the X-ray source unit 42, the collimator unit 44 and the control unit 46, and the X-ray detector arrangement 10 comprising the X-ray detector unit 12 and the rotation unit 14. The control unit 46 is configured to detect a spatial displacement between the X-ray source arrangement 40 and the X-ray detector arrangement 10. A moving assembly is provided performing a relative movement for bringing the X-ray detector arrangement 10 in alignment with the X-ray source arrangement 40 based on the detected spatial displacement.

In this embodiment, the moving assembly comprises a movable detector assembly 62 and a movable source assembly 64. However, the moving assembly may also be provided as a movable detector assembly, or as a movable source assembly.

The X-ray detector unit 12 is mounted to the movable detector assembly 64, which can move the X-ray detector unit 12 along x-, y- and z-axes. The rotation unit 14 is configured to rotate the X-ray detector 16 around the axis 20 perpendicular to the detector surface 18. The rotation action is indicated by a first round arrow $\alpha_D$. In an example, the X-ray detector 16 is arranged in a housing. In an example, the X-ray detector 16 rotates inside the housing. In another example, the X-ray detector 16 rotates together with the housing.

The X-ray source unit 42 is mounted to the moveable source assembly 62 with a slidable overhead carriage 66, a telescopic arm 68 and a housing 70. The X-ray source unit 42 is arranged inside the housing 70. The slidable overhead carriage 66 further comprises an x-track 72 and a y-track 74, which allows the movement of the X-ray source unit 42 along the x- and y-axes, respectively. In addition, the telescopic arm 68 can move the X-ray detector unit 12 upwards and downwards along the z-axis and can also rotate the X-ray detector unit around the z-axis, which is indicated by a second round arrow $\beta_S$. A pivot 76 is provided at the end of the telescopic arm 68, which allows a pivot movement of the X-ray source unit 42, which is indicated by a third round arrow $\alpha_S$. In other words, the moveable source assembly 62 enables a number of degrees of freedom so as to position the X-ray source unit 42 in a desired position relative to the region of interest 60.

The collimator unit 44 comprises an adjustable collimator opening 50 that defines the size and shape of the radiation field 48. The dimensions of the collimator opening can be adjusted, for example to be set to a portrait size. Moreover, the collimator unit 44 can be rotated to achieve a better match with a patient's anatomy.

In an example, the moveable source assembly 62 and the collimator configuration may be controlled by an operator, such as a lab technician, with a console 78, such as a computer. The dimensions of the adjustable collimator opening 50 may also be adjusted by using wheels or buttons.

In another example, the console 78 is not required. Instead, the geometry, such as size, shape and orientation, of the region of interest 60 may be detected by cameras, such as range cameras, optical cameras or ultrasound cameras. Anatomic landmarks may be derived from the image data to determine the desired position of the X-ray source unit relative to the region of interest 60 and the collimator configuration, such as dimensions of the opening and orientation of the collimator so as to adapt the radiation field 48 to the patient's anatomy.

In an example, the control unit 46 stores at least the collimator configuration parameters together with operating parameters of the X-ray detector arrangement 10.

Upon change of the position of the X-ray source arrangement 40 and/or the X-ray detector arrangement 10, the control unit 46 detects a spatial displacement and the moving assembly, i.e. the movable source assembly 62 and/or the movable detector assembly 64, performs a relative movement for bring the X-ray detector arrangement 10 in alignment with the X-ray source arrangement 40 based on the detected spatial displacement.

Further, the control unit 46 determines the geometric relationship between the collimation field 52 and the X-ray detector surface 18. Once a deviation is detected, for example, the collimation field 52 is not covered by the X-ray detector surface 18, for example, due to the adjustment of the collimator opening 50 or due to the rotation of the collimator unit 44, the control unit 46 determines an angular displacement according the collimator configuration and sends a further or updated signal of the rotation signal 22 to the rotation unit 14. In an example, the rotation signal 22 is transmitted via an electrical line and/or via fiber optics. In another example, the rotation signal 22 is provided as a wireless signal. Upon receiving the rotation signal 22, the rotation unit 14 rotates the X-ray detector 16 from such that the collimation field 52 is covered by the detector surface 18 again. During the rotation, the control unit 46 disables the generation of X-ray radiation. After the rotation, the X-ray generation is enabled again by the control unit 46.

In other words, the collimator unit 44 is configured to be a master unit, which controls the rotation position of the X-ray detector 16, i.e. a slave unit, by sending a master-to-slave signal, i.e. a rotation signal 22. The rotation signal 22 may also inform an angular displacement to the rotation unit 14. The rotation unit 14 rotates the X-ray detector 16 by the angular displacement so that the collimation field 52 is covered by the detector surface 18.

It is noted that the X-ray image acquisition system 100 in the exemplary embodiment is fixed to the walls of the examination room. However, also other X-ray imaging systems are provided, for example, a C-arm system with a patient lying on the examination table instead of standing.

Figure 5:
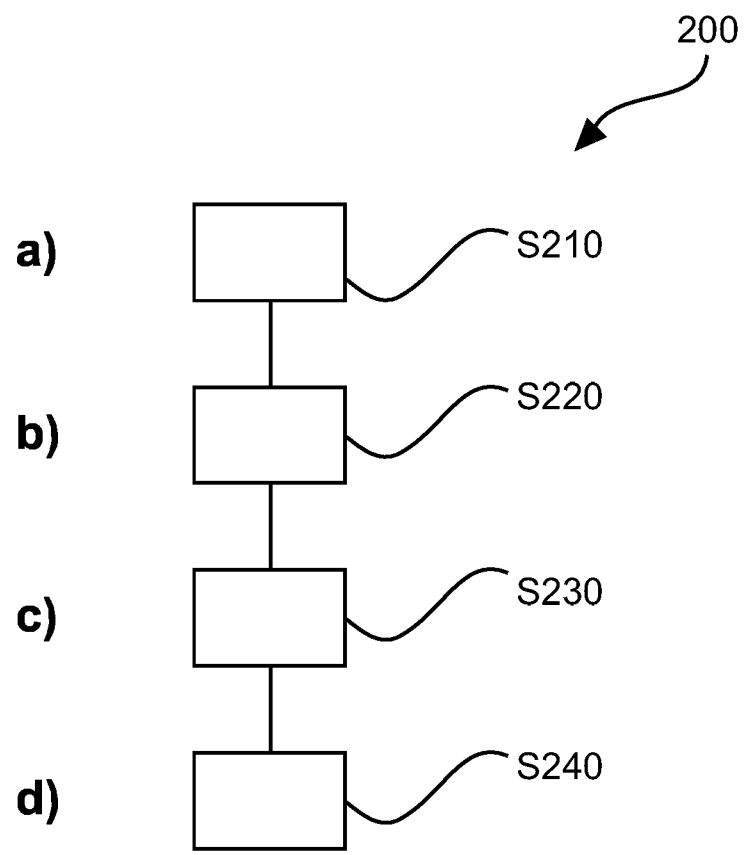
FIG. 5 shows basic steps of an example of a method for aligning a detector according to the present invention.

FIG. 5 shows a method 200 for aligning a detector, comprising the following steps:

In a first step S210, a configuration of a collimator of an X-ray source arrangement is adjusted.

In a second step S220, the collimator configuration is detected.

In a third step S230, a rotation signal is provide to a rotation unit. The rotation signal is based on the detected adjusted collimator configuration.

In a fourth step S240, an X-ray detector is rotated according to the rotation signal.

The first step S210 is also referred to as step a); the second step S220 is also referred to as step b); the third step S230 is also referred to as step c); and the fourth step S340 is referred to as step d).

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention. This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination of features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray image acquisition system, comprising:
an X-ray source configured to generate X-ray radiation;
a collimator having a configuration that includes an opening with adjustable dimensions to adjust a shape of the X-ray radiation passing through the opening;
an X-ray detector comprising a plurality of X-ray detecting elements arranged as a detector surface;
a controller configured to detect a collimation field on the detector surface based on the configuration of the collimator; and
a rotation unit configured to rotate the X-ray detector about an axis perpendicular to the detector surface, wherein the controller is configured to evaluate a geometric relationship between the collimation field and the detector surface and provide a rotation signal to the rotation unit to enable a rotation of the X-ray detector only when the collimation field is not fully covered by the detector surface, and wherein the X-ray radiation is disabled during the rotation of the X-ray detector.

2. The X-ray image acquisition system according to claim 1, wherein the rotation signal is a master-to-slave command signal, and the rotation unit is configured as a slave unit to receive the master-to-slave command signal.

3. The X-ray image acquisition system according to claim 1, wherein the X-ray detector is rotated from a first position to a second position, and an angular displacement between the second position and the first position is determined by the rotation signal.

4. The X-ray image acquisition system according to claim 3, wherein the X-ray detector has a shape with a first extension and a second extension, the first extension being larger than the second extension; and wherein in the second position, the first extension and the second extension are arranged in the angular displacement relative to the first extension and the second extension in the first position.

5. The X-ray image acquisition system according to claim 1, wherein the controller is configured to store configuration parameters of the collimator and operating parameters of the X-ray detector.

6. The X-ray image acquisition system according to claim 1, wherein the controller is configured to set maximum dimensions of the opening to ensure that the collimation field is smaller than the detector surface.

7. A method for acquiring an X-ray image, comprising:
generating X-ray radiation from an X-ray source;

adjusting a shape of the X-ray radiation passing through an opening in a collimator having a configuration that includes the opening with adjustable dimensions;

detecting the X-ray radiation by an X-ray detector comprising a plurality of X-ray detecting elements arranged as a detector surface;

detecting by a controller a collimation field on the detector surface based on the configuration of the collimator; and rotating the X-ray detector about an axis perpendicular to the detector surface, wherein the controller is configured to evaluate a geometric relationship between the collimation field and the detector surface and provide a rotation signal to enable a rotation of the X-ray detector only when the collimation field is not fully covered by the detector surface, and wherein the X-ray radiation is disabled during the rotation of the X-ray detector.

8. A non-transitory computer-readable medium having one or more executable instructions, which, when executed by a processor, cause the processor to perform a method for acquiring an X-ray image, comprising:

generating X-ray radiation from an X-ray source;

adjusting a shape of the X-ray radiation passing through an opening in a collimator having a configuration that includes the opening with adjustable dimensions;

detecting the X-ray radiation by an X-ray detector comprising a plurality of X-ray detecting elements arranged as a detector surface;

detecting by a controller a collimation field on the detector surface based on the configuration of the collimator; and rotating the X-ray detector about an axis perpendicular to the detector surface, wherein the controller is configured to evaluate a geometric relationship between the collimation field and the detector surface and provide a rotation signal to enable a rotation of the X-ray detector only when the collimation field is not fully covered by the detector surface, and wherein the X-ray radiation is disabled during the rotation of the X-ray detector.

* * * * *